US005569669A

United States Patent [19]

Guillaumet et al.

[11] Patent Number: 5,569,669

[45] Date of Patent: Oct. 29, 1996

[54] ALKYLAMINOINDANE COMPOUNDS

[75] Inventors: Gérald Guillaumet, St. Jean Leblanc; Marie-Claude Viaud, Orleans; Pierre Renard, Versailles; Gérard Adam, Le Mesnil Le Roi; Daniel-Henri Caignard, Paris; Béatrice Guardiola-Lemaitre, Saint-Cloud; Marie-Claire Rettori, Courbevoie, all of France

[73] Assignee: Adir et Compagnie, Courbevoie, France

[21] Appl. No.: 401,768

[22] Filed: Mar. 10, 1995

[30] Foreign Application Priority Data

Mar. 11, 1994 [FR] France .................................. 94 02813

[51] Int. Cl.$^6$ .................................................. A61K 31/38

[52] U.S. Cl. .......................... 514/432; 514/248; 514/249; 514/259; 514/307; 514/311; 514/434; 514/452; 514/456; 514/466; 514/469; 514/647; 514/651; 544/237; 544/283; 544/353; 546/149; 546/177; 549/15; 549/23; 549/365; 549/366; 549/407; 549/437; 549/467; 564/308; 564/348

[58] Field of Search ............................... 549/23, 15, 365, 549/366, 407, 437, 467; 544/237, 283, 353; 546/149, 177; 564/308, 348; 514/248, 249, 259, 307, 311, 432, 439, 452, 456, 466, 469, 647, 651

[56] References Cited

U.S. PATENT DOCUMENTS

| | | | |
|---|---|---|---|
| 5,140,039 | 8/1992 | DeBernardis et al. | 514/422 |
| 5,466,709 | 11/1995 | Schaus et al. | 514/432 |

*Primary Examiner*—Brian M. Burn

*Attorney, Agent, or Firm*—The Firm of Gordon W. Hueschen

[57] ABSTRACT

The invention relates to a compound selected from those of formula (I):

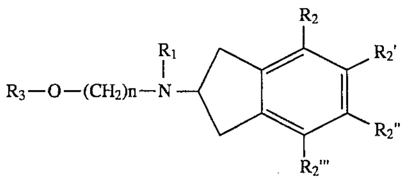

(I)

in which $R_1$, $R_2$, $R_{2'}$, $R_{2''}$, $R_{2'''}$, $R_3$ and n are as defined in the description, an optical isomer, and an addition salt thereof with a pharmaceutically-acceptable acid or base, and medicinal product containing the same useful for treating a mammal afflicted with a disorder associated to 5-$HT_{1A}$ or 5-$HT_{2C}$ receptors.

10 Claims, No Drawings

ALKYLAMINOINDANE COMPOUNDS

The present invention relates to new alkylaminoindane compounds, to a process for preparing them and to pharmaceutical compositions containing them.

Patent Application EP 286 278 already describes indanamine compounds of formula (A):

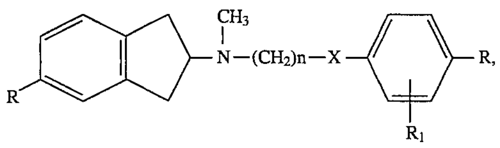

(A)

in which R, $R_1$, X and n are as defined in the Application EP 286 278, but only as antiarrhythmic agents.

The Applicant has discovered new alkylaminoindane compounds which display, surprisingly, a very strong affinity for serotonin receptors. They possess, in particular, an intense binding power not only for 5-$HT_{1A}$ receptors, but also for 5-$HT_{2C}$ receptors (formerly designated 5-$HT_{1C}$ receptors).

These features make them useful in therapy in disorders of the central nervous system (anxiety, depression, stress, psychoses, schizophrenia, pain, disorders of eating and sexual behavior and sleep disorders).

More specifically the subject of the present invention is the compounds of formula (I):

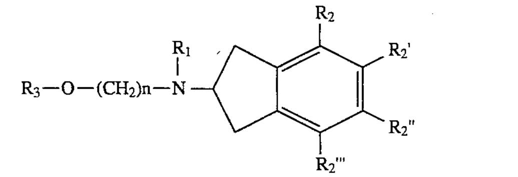

(I)

in which:

$R_1$ represents a hydrogen atom or a radical chosen from unsubstituted or substituted alkyl, cycloalkyl, cycloalkylalkyl, unsubstituted or substituted phenyl and unsubstituted or substituted phenylalkyl, $R_2$, $R_{2'}$, $R_{2''}$ and $R_{2'''}$ represent, independently of one another, a hydrogen atom or a radical chosen from halogen, unsubstituted or substituted alkyl and unsubstituted or substituted alkoxy, n represents an integer from 1 to 6, $R_3$ represents a group of formula (A):

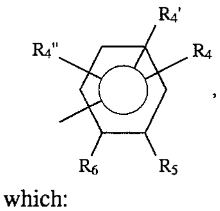

(A)

, in which:

$R_4$, $R_{4'}$ and $R_{4''}$ represent, independently of one another, a hydrogen atom or a radical chosen from halogen, unsubstituted or substituted alkyl and unsubstituted or substituted lower alkoxy, $R_5$ and $R_6$, together with the benzene ring which carries them, form a ring system $E_1$ chosen from: indene, naphthalene, benzothiophene, benzofuran, indole, benzimidazole, benzopyran, benzothiopyran, chroman, thiochroman, quinoline, isoquinoline, indazole, 2,3-dihydro-1,4-benzodithiin, quinoxaline, quinazoline, cinnoline, benzothiazole, benzisothiazole, benzoxazole, benzisoxazole, 2,3-dihydro-1,4-benzoxathiin, 1,4-benzoxazine, 1,4-benzothiazine, 1,3-benzodioxole, 1,3-benzodioxane, 1,4-benzodioxane and 1,4-benzodioxin, on the understanding that the portion of the ring system $E_1$ formed by $R_5$ and $R_6$ and the 2 carbon atoms of the benzene ring which carry them is:

unhydrogenated or partially hydrogenated, and unsubstituted or substituted with one or more radicals chosen from: halogen, hydroxyl, lower alkyl, unsubstituted or substituted alkoxy, lower alkoxycarbonyl and carboxyl, on the understanding that, except where otherwise stated, the terms "alkyl" and "alkoxy" mean linear or branched groups containing from 1 to 6 carbon atoms, the term "substituted" associated with "alkyl" and "alkoxy" radicals means "substituted with one or more radicals chosen from halogen, hydroxyl and alkoxy", the term "cycloalkyl" denotes a cyclic group having 3 to 8 carbon atoms, the term "substituted" associated with "phenyl" and "phenylalkyl" radicals means that these radicals may be substituted on the phenyl ring with one or more substituents chosen from alogen, alkyl, alkoxy, hydroxyl and polyhaloalkyl, their optical isomers and also their addition salts with a pharmaceutically acceptable acid or base.

In particular, alkyl radicals present in the different substituents of the formula (I) may be chosen from methyl, ethyl, n-propyl, isopropyl, n-butyl, isobutyl, sec-butyl, tert-butyl, pentyl and hexyl.

The alkoxy radicals present in the substituents of the formula (I) may be chosen from methoxy, ethoxy, n-propoxy, isopropoxy, n-butoxy, iso-butoxy, sec-butoxy, tert-butoxy, pentyloxy and hexyloxy.

The halogens present in the substituents of the formula (I) may be chosen from bromine, chlorine, fluorine and iodine.

The cycloalkyls present in substituents of the formula (I) may be chosen from cyclopropyl, cyclobutyl, cyclopentyl, cyclohexyl, cycloheptyl and cyclooctyl.

The groups $—(CH_2)_n—$ present in the formula (I) may be chosen from methylene, ethylene, trimethylene, tetramethylene, pentamethylene and hexamethylene.

Among pharmaceutically acceptable acids which may be used to form an addition salt with the compounds of the invention, hydrochloric, sulfuric, phosphoric, tartaric, malic, maleic, fumaric, oxalic, methanesulfonic, ethanesulfonic, camphoric and citric acid may be mentioned as examples and without implied limitation.

Among pharmaceutically acceptable bases which may be used to salify the compounds used according to the invention, sodium hydroxide, potassium hydroxide, triethylamine, diethylamine, ethanolamine, arginine, lysine and diethanolamine may be mentioned as examples and without implied limitation.

The invention relates more especially to the compounds of formula (I) in which $R_5$ and $R_6$, together with the benzene ring which carries them, form a ring system $E_1$ chosen from naphthalene, benzopyran, benzothiopyran, chroman, thiochroman and benzodioxane.

For example, the invention relates to the compounds of formula (I) in which $R_5$ and $R_6$, together with the benzene ring which carries them, form a ring system $E_1$ chosen from thiochroman, chroman and benzodioxane.

The invention also encompasses the process for preparing the compounds of formula (I), wherein a hydroxylated derivative of formula (II):

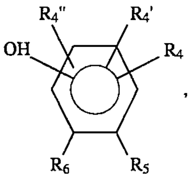

(II)

in which $R_4$, $R_{4'}$, $R_4''$, $R_5$ and $R_6$ are as defined in the formula (I), is reacted with a dihaloalkyl of formula (III):

$$X—(CH_2)n—X' \quad (III)$$

in which X and X' are halogen atoms and n is as defined in the formula (I), to give a compound of formula (IV):

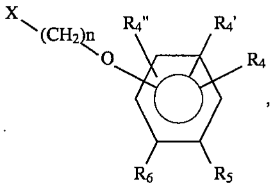

(IV)

in which n, X, $R_4$, $R_{4'}$, $R_4''$, $R_5$ and $R_6$ are as defined above, said compound of formula (IV) is reacted with an aminoindane of formula (V):

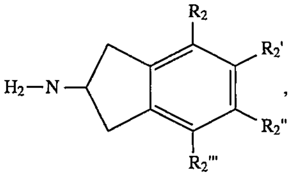

(V)

in which $R_2$, $R_{2'}$, $R_{2''}$ and $R_{2'''}$ are as defined in the formula (I), to give a compound of formula (Ia):

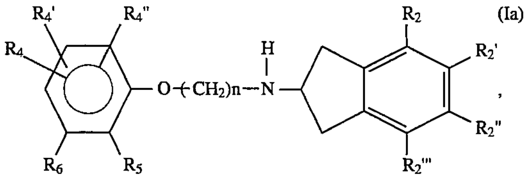

(Ia)

in which $R_2$, $R_{2'}$, $R_2''$, $R_2'''$, $R_4$, $R_{4'}$, $R_4''$, $R_5$, $R_6$ and n are as defined above, it being possible for said compound of formula (Ia) to be brought into contact with a haloalkyl of formula (VI):

$R_1'—X''$(VI), in which X" is a halogen atom and $R_1$, has the same meaning as $R_1$ as defined in the formula (I) except for hydrogen, to give a compound of formula (Ib):

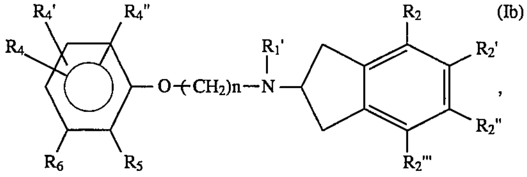

(Ib)

in which $R_1'$, $R_2$, $R_{2'}$, $R_{2''}$, $R_{2'''}$, $R_4$, $R_{4'}$, $R_{4''}$, $R_5$, $R_6$ and n are as defined above, the compounds of formula (Ia) and (Ib) constituting the set of compounds of formula (I) which can, if so desired, be purified according to one or more purification methods chosen from crystallization, chromatography on a silica column, extraction, filtration and passage through charcoal and/or resin, separated, where appropriate, in pure form or in the form of a mixture, into their possible optical isomers, and/or salified with a pharmaceutically acceptable acid or base.

The invention also encompasses the variants of the process described above, on the understanding that they are capable of being carried out by a person skilled in the art.

The starting materials used in the process described above are either commercially available, or readily accessible to a person skilled in the art on the basis of the literature.

The Applicant discovered that the compounds of the invention possessed very advantageous pharmacological properties.

The compounds of the invention display, surprisingly, a very strong affinity for serotoninergic receptors, and in particular an intense antagonist power with respect to $5\text{-}HT_{1A}$ and $5\text{-}HT_{2C}$ receptors.

Tests of binding to $5\text{-}HT_{1A}$ and $5\text{-}HT_{1C}$ receptors have, in effect, shown that the compounds of the invention behave as potent ligands for $5\text{-}HT_{1A}$ and $5\text{-}HT_{1C}$ serotoninergic receptors (Example B of the present application).

The antagonist activity of the compounds of the invention has been demonstrated in vitro, and manifests itself in vivo in a very strong anxiolytic activity (so-called light/dark cage test in mice, Example F in the present application) combined with an exceptional antidepressant activity (escape failure test in rats, Example E of the present application).

As a result, the compounds of general formula (I) and their physiologically tolerable salts possess advantageous pharmacological and therapeutic properties, in particular anxiolytic and antidepressant properties and properties of regulating sleep disorders.

The compounds of the present invention may thus be used in the treatment and prevention of disorders associated with $5\text{-}HT_{1A}$ or $5\text{-}HT_{2C}$ receptors. For example, they may be used in the treatment and prevention of stress, anxiety, depression, psychoses, schizophrenia, pain, disorders of eating and sexual behavior and sleep disorders.

Moreover, the compounds of the invention surprisingly potentiate the effects of known antidepressants and enable them to become effective immediately (disappearance of the generally observed two-week latency period).

The subject of the present invention is also pharmaceutical compositions containing a compound of formula (I), or one of its physiologically tolerable salts, in combination with one or more pharmaceutically acceptable excipients or vehicles.

Among the pharmaceutical compositions according to the invention, there may be mentioned, as examples and without implied limitation, those which are suitable for oral, rectal, nasal or parenteral administration, and in particular tablets, dragees, capsules including hard gelatin capsules, packets, sachets, granules, pills, pellets, suppositories, creams, ointments, aerosols, skin gels and injectable solutions or those to be taken by mouth.

The dosage varies from one individual to another according to the patient's age, weight and sex, the chosen administration route and the nature and intensity of the complaint. Doses used range between 0.1 and 100 mg daily, divisible into 1 to 3 portions per 24 h, more especially 1 to 10 mg daily, for example 5 mg daily.

The examples which follow illustrate the invention and in no way limit it.

EXAMPLE 1

8-{4-[(N-indan)-2-yl)amino]butyloxy}thiochroman

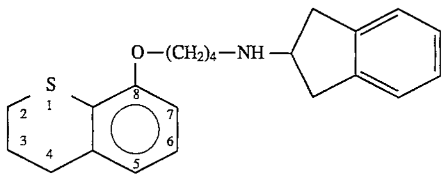
Example 1

Stage A: 8-(4-bromobutyloxy)thiochroman 300 mg of 8-hydroxythiochroman (as described in Patent EP 571,243) are dissolved in 3 $cm^3$ of N,N-dimethylformamide under argon. 430 mg (1.985 mmol) of 1,4-dibromobutane diluted in 3 $cm^3$ of N,N-dimethylformamide are added. 750 mg of potassium carbonate are then added using a spatula. The mixture is brought to 65° C. under argon and with stirring for 3 h 30 min. The N,N-Dimethylformamide is evaporated off. The residue is taken up with $H_2O$ and the product is extracted with dichloromethane before being purified on a silica column (eluent: ether/petroleum ether, 15:85). 240 mg of white crystals of 8-(4-bromobutyloxy)thiochroman are recovered.

Stage B: 8-{4-[(N-indan-2-yl)amino]butyloxy}thiochroman

Under argon, 1 g (3.32 mmol) of bromo compound prepared in Stage A, 850 mg (4.98 mmol) of 2-aminoindane hydrochloride and 2.15 g (16.60 mmol) of N,N-diisopropylethylamine are dissolved in 40 $cm^3$ of acetonitrile. The mixture is kept refluxing for 40 hours. The solvent is evaporated off. The residue is taken up with water and the product is extracted with dichloromethane. The organic phase is dried over magnesium sulfate. After concentration, the product is purified on a normal silica column (eluent: methanol/dichloromethane, 5:95). 630 mg of a highly colored solid are recovered and recrystallized in ethanol.

Yield: 54% Melting point: 179°–180° C. IR(KBr)$cm^{-1}$: 3600–3200 (νNH) 1255 (νC—O) MS(m/e): 354 (M+1) $^1$H NMR 300 MHz ($CDCl_3$): 1.70 (s, 1H, NH); 1.85–2.15 (m, 6H, $CH_2$); 2.75 (t, 2H, J=5.9 Hz, $CH_2Ar_1$); 2.83–2.89 (m, 2H, $CH_2S$); 3.07 (t, 2H, J=7.4 Hz, $CH_2$—N); 3.23 (dd, 2H, $J_1$=15.4 Hz, $J_2$=7.4 Hz, 2×$Ar_2$CHCHN); 3.33 (dd, 2H, $J_1$=15.4 Hz, $J_2$=7.4 Hz, 2×$Ar_2$CHCHN); 3.93 (quintet, 1H, J=7.4 Hz, CHN); 3.99 (t, 2H, J=5.9 Hz, O—$CH_2$); 6.58 (d, 1H, J=7.4 Hz, Arom); 6.63 (d, 1H, J=7.4 Hz, Arom); 6.89 (t, 1H, J=7.4 Hz, Arom); 7.09–7.18(m, 4H, Arom).

EXAMPLE 2

8-{3-[(N-indan-2-yl)amino]propyloxy}thiochroman

Stage A: 8-(3-bromopropyloxy)thiochroman

Using the same procedure as that described in Stage A of Example 1, but replacing 1,4-dibromobutane by 1,3-dibromopropane, the compound of the title is obtained.

Stage B: {3-[(N-indan-2-yl-8)aminopropyloxy]}thiochroman

Under argon, 1 g (3.48 mmol) of bromo compound prepared in Stage A, 890 mg (5.22 mmol) of 2-aminoindane hydrochloride and 2.25 g (17.41 mmol) of N,N-diisopropylethylamine are dissolved in 35 $cm^3$ of acetonitrile. The mixture is kept refluxing for 40 hours. The solvent is evaporated off. The residue is taken up with $H_2O$ and the product is then extracted with dichloromethane. The organic phase is dried over magnesium sulfate. After concentration, the product is purified on a normal silica column (eluent: methanol/dichloromethane, 5:95). 740 mg of a highly colored oil are recovered, the fumarate of which product is made.

Yield: 63% Melting point (fumarate): 170° C. IR(film)$cm^{-1}$: 3600–3200 (νNH) 1250 (νC—O) MS(m/e): 340 (M+1) $^1$H NMR 300 MHz ($CDCl_3$): 1.70 (s, 1H, NH); 1.96–2.11 (m, 4H, $CH_2$); 2.73–2.99 (m, 8H, $CH_2Ar_1$, $CH_2S$, $CH_2S$, $CH_2N$, 2×$Ar_2$CHCHN); 3.16 (dd, 2H, $J_1$=15.4 Hz, $J_2$=6.6 Hz, 2×$Ar_2$CHCHN); 3.64 (quintet, 1H, J=6.6 Hz, CHN); 4.08 (t, 2H, J=5.9 Hz, O—$CH_2$); 6.60–6.68 (m, 2H, Arom); 6.90 (t, 1H, J=7.4 Hz, Arom); 7.08–7.20 (m, 4H, Arom).

EXAMPLE 3

8-{2-[(N-indan-2-yl)amino]ethoxy}thiochroman

Stage A: 8-(2-bromoethoxy)thiochroman

Using the same procedure as that described in Stage A of Example 1, but replacing 1,4-dibromobutane by 1,2-dibromoethane, the compound of the title is obtained.

Stage B: 8-{2-[(N-indan-2-yl)amino]ethoxy}thiochroman

Under argon, 500 mg (1.83 mmol) of bromo compound prepared in Stage A, 470 mg (2.75 mmol) of 2-aminoindan hydrochloride and 1.2 g (9.15 mmol) of N,N-diisopropylethylamine are dissolved in 15 $cm^3$ of acetonitrile. The mixture is kept refluxing for 40 hours.

The solvent is evaporated off. The residue is taken up with $H_2O$ and the product is extracted with dichloromethane. The organic phase is dried over magnesium sulfate. After concentration, the product is purified on a normal silica column (eluent: methanol/dichloromethane, 1:99). 310 mg of a highly colored solid are recovered.

Yield: 52% Melting point (fumarate): 173° C. IR(KBr)$cm^{-1}$: 3600–3200 (νNH) 1250 (νC—O) MS(m/e): 326 (M+1) $^1$H NMR 300 MHz ($CDCl_3$): 1.70 (s, 1H, NH); 2.02–2.13 (m, 2H, $CH_2$); 2.77–2.88 (m, 4H, $CH_2Ar$, 2×$Ar_2$CHCHN); 2.94–3.02 (m, 2H, $CH_2S$); 3.08 (t, 2H, J=5.2 Hz, $CH_2N$); 3.21 (dd, 2H, $J_1$=15.5 Hz, $J_2$=6.9 Hz, 2×$Ar_2$CHCHN); 3.71 (quintet, 1H, J=6.9 Hz, CHN); 4.14 (t, 2H, J=5.2 Hz, CH—O); 6.63–6.71 (m, 2H, Arom); 6.92 (t, 1H, J=7.7 Hz, Arom); 7.09–7.23 (m, 4H, Arom).

EXAMPLE 4

8-{3-[(n-propyl-n-indan-2-yl)amino]propyloxy}thiochroman

Under argon, 180 mg (5.30×$10^{-4}$ mol) of 8-{3-[(n-indan-2-yl)amino]propyloxy}thiochroman prepared according to Example 2, 540 mg (3.18 mmol) of 1-iodopropane and 200 mg (1.59 mmol) of N,N-diisopropylethylamine are dissolved in 2 $cm^3$ of dimethylformamide. The mixture is maintained at 60° C. for 24 hours and the solvent is then evaporated off. The residue is taken up with water and the product is extracted with dichloromethane. The organic phase is dried over magnesium sulfate. After concentration, the product is purified on a normal silica column (eluent: 100%.ethyl acetate). 170 mg of a beige solid are obtained and recrystallized in cyclohexane.

Yield: 84% Melting point: 68°–69° C. IR(KBr)$cm^{-1}$: 1260 (νC—O) MS(m/e): 382 (M+1) $^1$H NMR 300 MHz ($CDCl_3$): 0.89 (t, 3H, J=7.3Hz, $CH_3$); 1.46–1.61 (m, 2H, $CH_2$); 1.92–2.13 (m, 4H, $CH_2$); 2.49–2.57 (m, 2H, $CH_2$); 2.76–3.09 (m, 10H, $CH_2$); 3.68 (quintet, 1H, J=7.9 Hz, CH—N); 4.06 (t, 2H, J=6.1 Hz, $CH_2$—O); 6.62–6.68 (m, 2H, Arom); 6.92 (t, 1H, J=7.9 Hz, Arom); 7.09–7.19 (m, 4H, Arom).

EXAMPLES 5 to 8:

Using the procedure described in Examples 1 to 4, but replacing 8-thiochromanol by 1-hydroxynaphthalene (as described in J. Labelled Compd. Radiopharm.; 85; Vol. 22 (11 ); pp. 1149–54), the following compounds are obtained:

EXAMPLE 5

1-{4-[(n-indan-2-yl)amino]butyloxy}naphthalene

EXAMPLE 6

1-{3-[(n-indan-2-yl)amino]propyloxy}naphthalene

EXAMPLE 7

1-{2-[(n-indan-2-yl)amino]ethoxy}naphthalene

EXAMPLE 8

1-{3-[(n-propyl-n-indan-2-yl)amino]propyloxy}naphthalene

EXAMPLES 9 to 12:

Using the procedure described in Examples 1 to 4, but replacing 8-thiochromanol by 8-hydroxyquinoline (as described in J. Mater. Chem.; 91; Vol. 1(3); pp. 327–30), the following compounds are obtained:

EXAMPLE 9

8-{4-[(n-indan-2-yl)amino]butyloxy}quinoline

EXAMPLE 10

8-{3-[(n-indan-2-yl)amino]propyloxy}quinoline

EXAMPLE 11

8-{2-[(n-indan-2-yl)amino]ethoxy}quinoline

EXAMPLE 12

8-{3-[(n-propyl-n-indan-2-yl)amino]propyloxy}quinoline

EXAMPLES 13 to 16:

Using the procedure described in Examples 1 to 4, but replacing 8-hydroxythiochroman by 8-hydroxy-2H-benzopyran (as described in Chem. Pharm. Bull.; 86; Vol. 34(5); pp. 2024–36), the following compounds are obtained:

EXAMPLE 13

8-{4-[(n-indan-2-yl)amino]butyloxy}-2H-benzopyran

EXAMPLE 14

8-{3-[(n-indan-2-yl)amino]propyloxy}-2H-benzopyran

EXAMPLE 15

8-{2-[(n-indan-2-yl)amino]ethoxy}-2H-benzopyran

EXAMPLE 16

-8-{3-[(n-propyl-n-indan-2-yl)amino]propyloxy}-2H-benzopyran

EXAMPLES 17 to 20:

Using the procedure described in Examples 1 to 4, but replacing 8-hydroxythiochroman by 8-hydroxychroman (as described in Chem. Pharm. Bull.; 87; Vol. 35(2); pp. 632–41), the following compounds are obtained:

EXAMPLE 17

8-{4-[(n-indan-2-yl)amino]butyloxy}chroman

EXAMPLE 18

8-{3-[(n-indan-2-yl)amino]propyloxy}chroman

EXAMPLE 19

8-{2-[(n-indan-2-yl)amino]ethoxy}chroman

Melting point: 170°–172° C.

EXAMPLE 20

8-{3-[(n-propyl-n-indan-2-yl)amino]propyloxy}chroman

EXAMPLES 21 to 24:

Using the procedure described in Examples 1 to 4, but replacing 8-hydroxythiochroman by 8-hydroxy-1,2,3,4-tetrahydroisoquinoline (as described in J. Med. Chem.; 87; Vol. 30(112); pp. 2208–16), the following compounds are obtained:

EXAMPLE 21

8-{4-[(n-indan-2-yl)amino]butyloxy}-1,2,3,4-tetrahydroisoquinoline

EXAMPLE 22

8-{3-[(n-indan-2-yl)amino]propyloxy}-1,2,3,4-tetrahydroisoquinoline

EXAMPLE 23

8-(2-[(n-indan-2-yl)amino]ethoxy}-1,2,3,4-tetrahydroisoquinoline

EXAMPLE 24

8-(3-[(n-propyl-n-indan-2-yl)amino]propyloxy}-1,2,3,4-tetrahydroisoquinoline

EXAMPLES 25 to 28:

Using the procedure used in Examples 1 to 4, but replacing 8-hydroxythiochroman by 5-hydroxyquinoxaline (as described in Recl. Trav. Chim. Pays-Bas; 76; Vol. 95(12); pp. 285–9), the following compounds are obtained:

EXAMPLE 25

5-{4-[(n-indan-2-yl)amino]butyloxy}quinoxaline

EXAMPLE 26

5-{3-[(n-indan-2-yl)amino]propyloxy}quinoxaline

EXAMPLE 27

5-{2-[(n-indan-2-yl)amino]ethoxy}quinoxaline

EXAMPLE 28

5-{3-[(n-propyl-n-indan-2-yl)amino]propyloxy}quinoxaline

EXAMPLES 29 to 32:

Using the procedure described in Examples 1 to 4, but replacing 8-hydroxythiochroman by 8-hydroxyquinazoline (as described in Text. Chem. Color.; 92; Vol. 24(9); pp. 66–71), the following compounds are obtained:

EXAMPLE 29

8-{4-[(n-indan-2-yl)amino]butyloxy}quinazoline

EXAMPLE 30

8-{3-[(n-indan-2-yl)amino]propyloxy}quinazoline

EXAMPLE 31

8-{2-[(n-indan-2-yl)amino]ethoxy}quinazoline

EXAMPLE 32

8-{3-[(n-propyl-n-indan-2-yl)amino]propyloxy}quinazoline

EXAMPLES 33 to 36:

Using the procedure described in Examples 1 to 4, but replacing 8-hydroxythiochroman by 8-hydroxycinnoline (as described in Tetrahedron; 78; Vol. 34(7); pp. 941–6), the following compounds are obtained:

EXAMPLE 33

8-{4-[(n-indan-2-yl)amino]butyloxy}cinnoline

EXAMPLE 34

8-{3-[(n-indan-2-yl)amino]propyloxy}cinnoline

EXAMPLE 35

8-{2-[(n-indan-2-yl)amino]ethoxy}cinnoline

EXAMPLE 36

8-{4-[(n-propyl-n-indan-2-yl)amino]butyloxy}cinnoline

EXAMPLES 37 to 40:

Using the procedure described in Examples 1 to 4, but replacing 8-hydroxythiochroman by 8-hydroxy-1,3-benzodioxane (as described in Patent Application EP 103,173), the following compounds are obtained:

EXAMPLE 37

8-{4-[(n-indan-2-yl)amino]butyloxy}-1,3-benzodioxane

EXAMPLE 38

8-{3-[(n-indan-2-yl)amino]propyloxy}-1,3-benzodioxane

EXAMPLE 39

8-{2-[(n-indan-2-yl)amino]ethoxy}-1,3-benzodioxane

EXAMPLE 40

8-{4-[(n-propyl-n-indan-2-yl)amino]butyloxy}1,3-benzodioxane

EXAMPLES 41 to 45:

Using the procedure described in Examples 1 to 4, but replacing 8-hydroxythiochroman by 7-hydroxy-1H-indene (as described in J. Am. Chem. Soc.; 93; Vol. 115(17); pp. 7653–64), the following compounds are obtained:

EXAMPLE 41

7-{4-[(n-indan-2-yl)amino]butyloxy}indene

EXAMPLE 42

7-{3-{(n-indan-2-yl)amino]propyloxy}indene

EXAMPLE 43

7-{2-[(n-indan-2-yl)amino]ethoxy}indene

EXAMPLE 44

7-{4-[(n-propyl-n-indan-2-yl)amino]butyloxy}indene

EXAMPLES 45 to 48:

Using the procedure described in Examples 1 to 4, but replacing 8-hydroxythiochroman by 4-hydroxy-1,3-benzodioxole (as described in J. Chem. Soc. Faraday Trans. 2; 79;

Vol. 75(12); pp. 1637–42), the following compounds are obtained:

EXAMPLE 45

4-{4-[(n-indan-2-yl)amino]butyloxy}-1,3-benzodioxole

EXAMPLE 46

4-{3-[(n-indan-2-yl)amino]propyloxy}-1,3-benzodioxole

EXAMPLE 47

4-{2-[(n-indan-2-yl)amino]ethyloxy}-1,3-benzodioxole

EXAMPLE 48

4-{4-[(n-propyl-n-indan-2-yl)amino]butyloxy}-1,3-benzodioxole

EXAMPLES 49 to 52:

Using the procedure described in Examples 1 to 4, but replacing 8-hydroxythiochroman by 4-hydroxy-2,3-dihydrobenzofuran (as described in Hétérocycles; 92; Vol. 34(7); pp. 1353–64), the following compounds are obtained:

EXAMPLE 49

7-{4-[(n-indan-2-yl)amino]butyloxy}benzofuran

EXAMPLE 50

7-{3-[(n-indan-2-yl)amino]propyloxy}benzofuran

EXAMPLE 51

7-{2-[(n-indan-2-yl)amino]ethoxy}benzofuran

EXAMPLE 52

7-{4-[(n-propyl-n-indan-2-yl)amino]butyloxy}benzofuran

EXAMPLES 53 to 56:

Using the procedure described in Examples 1 to 4, but replacing 8-hydroxythiochroman by 5-hydroxy-2,3-dihydro-1,4-benzoxathiin (as described in U.S. Pat. No. 3,636,047), the following compounds are obtained:

EXAMPLE 53

5-{4-[(n-indan-2-yl)amino]butyloxy}-2,3-dihydro-1,4-benzoxathiin

EXAMPLE 54

5-{3-[(n-indan-2-yl)amino]propyloxy}-2,3-dihydro-1,4-benzoxathiin

EXAMPLE 55

5-{2-[(n-indan-2-yl)amino]ethoxy}-2,3-dihydro-1,4-benzoxathiin

EXAMPLE 56

5-(3-[(n-propyl-n-indan-2-yl)amino]propyloxy}-2,3-dihydro-1,4-benzoxathiin

EXAMPLES 57 to 60:

Using the procedure described in Examples 1 to 4, but replacing 8-hydroxythiochroman by 5-hydroxy-2,3-dihydro-1,4-benzodithiin (as described in U.S. Pat. No. 3,636,047), the following compounds are obtained:

EXAMPLE 57

5-{4-[(n-indan-2-yl)amino]butyloxy}-2,3-dihydro-1,4-benzodithiin

EXAMPLE 58

5-{3-[(n-indan-2-yl)amino]propyloxy}-2,3-dihydro-1,4-benzodithiin

EXAMPLE 59

5-{2-[(n-indan-2-yl)amino]ethoxy}-2,3-dihydro-1,4-benzodithiin

EXAMPLE 60

5-{3-[(n-propyl-n-indan-2-yl)amino]propyloxy}-2,3-dihydro-1,4-benzodithiin

EXAMPLES 61 to 64:

Using the procedure described in Examples 1 to 4, but replacing 8-hydroxythiochroman by 5-hydroxy-1,4-benzodioxane, the following compounds are obtained:

EXAMPLE 61

5-{4-[(n-indan-2-yl)amino]butyloxy}-1,4-benzodioxane

EXAMPLE 62

5-{3-[(n-indan-2-ylamino]propyloxy}-1,4-benzodioxane

EXAMPLE 63

5-{2-[(n-indan-2-yl)amino]ethoxy}-1,4-benzodioxane

Stage A: 5-methoxy-1,4-benzodioxane

A mixture of dibromoethane (10.73 g, 77 mmol) and cetyltrimethylammonium bromide (0.291 g, 0.8 mmol) in 5 $cm^3$ of water is brought to reflux. A solution of 3-methoxycatechol (5 g, 35.7 mmol) in 20N sodium hydroxide (NaOH, 4 g in 5 $cm^3$ of water) is added slowly. The mixture is stirred at the reflux for 12 hours and then, after cooling and extraction with ether, purification on a silica column (eluent: petroleum ether/ether, 9:1) enables 7.4 g of a colorless oil to be isolated Yield: 80%

Stage B: 5-hydroxybenzodioxane

At 0° C., boron tribromide (5.6 $cm^3$) is added slowly to a solution of 5-methoxy-1,4-benzodioxane (5 g, 30.1 mmol) in 25 $cm^3$ of $CH_2Cl_2$. The mixture is stirred at 0° C. for 15 min, the solution is then hydrolysed with 10 $cm^3$ of water and the product is extracted with $CH_2Cl_2$. Purification on a silica column (eluent: 100% $CH_2Cl_2$) enables 4.49 g of a colorless oil to be obtained.

Yield: 95%

Stage C: 5-(3-bromoethyloxy)benzodioxane 730 mg (4.80 mmol) of 5-hydroxybenzodioxane and 1.80 g (9.60 mmol, 0.82 $cm^3$) of 1,2-dibromoethane are brought into solution at 100° C. The mixture is cooled and 4.5 $cm^3$ (7.20 mmol) of 1.6N aqueous sodium hydroxide solution are then added dropwise. After 24 hours at 100° C., the mixture is cooled and taken up with 35 $cm^3$ of 2N aqueous sodium hydroxide. The product is extracted with $CH_2Cl_2$ and then purified on a silica column (eluent: 100% $CH_2Cl_2$). 700 mg of a white solid are recovered.

Melting point: 86° C.

Yield: 56%-

Stage D: 5-{2-[(n-indan-2-yl)amino]ethoxy}-1,4-benzodioxane

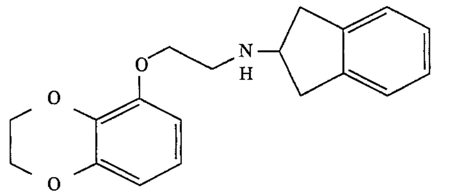

Example 63

50 mg ($1.93\times10^{-4}$ mol) of bromo compound obtained in the preceding stage, 40 mg ($2.89\times10^{-4}$ mol) of 2-aminoindane hydrochloride and 125 mg ($9.65\times10^{-4}$ mol) of N,n-diisopropylethylamine are dissolved in 2.5 $cm^3$ of acetonitrile. After 40 hours at the reflux, the solvent is evaporated off. The residue is taken up with $H_2O$ and the product is extracted with $CH_2Cl_2$. After purification on a silica column (eluent: 100% $CH_2Cl_2 \rightarrow MeOH/CH_2Cl_2$, 1:99), 40 mg of a highly colored oil are obtained, the fumarate of which product is made.

Yield: 66%

EXAMPLE 64

5-{3-[(n-propyl-n-indan-2-yl)amino]propyloxy}-1,4-benzodioxane

EXAMPLE 65

8-{3-[(n-METHYL-n-indan-2-yl)amino]propyloxy}thiochroman

Under argon, 1 g (2.95 mmol) of 8-(3-[(n-indan-2-yl)amino]propyloxy}thiochroman prepared according to Example 2, 0.67 cm 3 (740 mg, 11.78 mmol) of glacial acetic acid and 740 mg (11.78 mmol) of sodium cyanoborohydride are dissolved in 15 $cm^3$ of anhydrous methanol. The mixture is cooled in an ice bath. Using a dropping funnel, 0.96 $cm^3$ (354 mg, 11.78 mmol) of 37% formaldehyde in water dissolved in 15 $cm^3$ of methanol is added dropwise. The mixture is left stirring for 3 hours at room temperature, and 10 $cm^3$ of saturated $K_2CO_3$ solution are then added. The methanol is driven off under vacuum. The residue is taken up with $H_2O$ and the product is extracted with AcOEt. After purification on a normal silica column (eluent: 100% $CH_2Cl_2 \rightarrow MeOH/CH_2Cl_2$, 5:95), 940 mg of a solid are obtained and recrystallized in isopropanol.

Yield: 90% Melting point: 75°–76° C.

EXAMPLE 66

8-{2-[(n-propyl-n-indan-2-yl)amino]ethoxy}thiochroman

Melting point: 164° C.

PHARMACOLOGICAL STUDY OF THE COMPOUNDS OF THE INVENTION

EXAMPLE A

Study of Acute Toxicity

The acute toxicity was evaluated after oral administration of increasing doses (0.1, 0.25, 0.50, 0.75 and 1 $g.kg^{-1}$) of the products of the invention to groups of five mice (20±2 grams). The animals were observed at regular intervals during the first day and daily during the two weeks following the treatment. It is apparent that the compounds of the invention are completely nontoxic at the doses tested. No death is observed after administration of a dose of 1 $g.kg^{-1}$. No disorders are noted after administration of this dose.

EXAMPLE B

Measurement of the Affinity of the Compounds of the Invention for $5\text{-}HT_{1A}$ Receptors

PROTOCOL:

The in vitro affinity of the compounds of the invention for $5\text{-}HT_{1A}$ serotoninergic receptors was determined by measuring the displacement of [$^3$H]-8-hydroxy-2-(di-n-propylamino)tetralin [or [$^3$H]-8-OH-DPAT], a selective agonist for this receptor, on rat hippocampus preparations.

RESULTS:

The compounds of general formula (I) prove to be very potent ligands for $5\text{-}HT_{1A}$ receptors, with affinity constants of the order of nanomolar.

EXAMPLE C

Measurement of the Affinity of the Compounds of the Invention for $b_1$, $b_2$, $D_1$, $D_2$, $5\text{-}HT_{1C}$, $5\text{-}HT_{1D}$, $5\text{-}HT_2$ and $5\text{-}HT_3$ Receptors

PROTOCOL:

The in vitro affinity of the compounds of the invention was determined:

for $\beta_1$ adrenergic receptors, by measuring the displacement of dihydroalprenolol on rat frontal cortex preparations, for $\beta_2$ adrenergic receptors, by measuring the displacement of dihydroalprenolol on rat lung parenchyma preparations, for $D_1$ dopaminergic receptors, by measuring the displacement of SCH 23390 on rat striatum preparations, for $D_2$ dopaminergic receptors, by measuring the displacement of raclopride on rat striatum preparations, for $5\text{-}HT_{1C}$ serotoninergic receptors, by measuring the displacement of n-methylmesulergine on rat frontal cortex and hippocampus preparations, for $5\text{-}HT_{1D}$ serotoninergic receptors, by measuring the displacement of 5-OH-tryptamine on rat cortex, striatum and globus pallidus preparations, for $5\text{-}HT_2$ serotoninergic receptors, by measuring the displacement of aminoiodoketanserin on rat frontal cortex preparations, for $5\text{-}HT_3$ serotoninergic receptors, by measuring the displacement of BRL 43694 on rat aera postrema preparations.

RESULTS:

Some compounds of the invention display a markedly lower affinity for $\beta_1$, $\beta_2$, $D_1$, $D_2$, $5\text{-}HT_{1D}$, $5\text{-}HT_2$ and $5\text{-}HT_3$ receptors than for $5\text{-}HT_{1C}$ receptors.

EXAMPLE D

Evaluation of the $5\text{-}HT_{1A}$ Receptor-Antagonist Activity of the Compounds of the Invention

PROTOCOL:

Evaluation of the $5\text{-}HT_{1A}$ receptor-antagonist activity of the compounds of the invention was carried out by stimulating adenylate cyclase with 10 mM forskolin in the presence of the test compound and in the absence or presence of 0.1 mM 8-hydroxy-2-(di-n-propylamino)tetralin (8-OH-DPAT). The products of the invention were tested for concentration ranges extending from 10 nM to 10 mM.

RESULTS:

The compounds of formula (I) competitively counteract ($IC_{50}$<50 nM) the inhibition of adenylate cyclase induced by 8-OH-DPAT (0.1 mM) in rat hippocampus homogenates, reflecting a strong 5-$HT_{1A}$ receptor-antagonist activity.

EXAMPLE E

Study of the Antidepressant Activity of the Compounds of the Invention

PRINCIPLE:

Study of the products is carried out on the model of "learned resignation", which consists in inducing in the animal, by a series of uncontrollable aversion events, a deficiency in executing subsequent avoidance tasks.

PROTOCOL:

This test was developed by Sherman A. D., Sacquitne J. L., and Petty F. (Pharmacol. Biochem. Behav., 1982, 16, 449–454). We use male Wistar rats weighing between 180 and 200 grams. The animals are kept in an animal house for one week before the test, in plastic boxes, in groups of 10, at an ambient temperature of 21° C.±1° C. with free access to water and food. The animals are then isolated in small boxes and are subjected to 60 unavoidable electric shocks (0.8 mA every minute±15 seconds). A control group of rats does not receive electric shocks. The animals' capacity to achieve an avoidance learning (passage from one compartment to another in order to avoid electric shocks) is assessed 48 hours later and over 3 consecutive days. During the learning sessions, the animals undergo two tests per minute over 15 minutes. The number of failures to escape is noted for each rat. The animals are treated (i.p.: 0.5 $cm^3$/100 g) 6 hours after the unavoidable shocks and on 4 consecutive days, in the morning 30 minutes before the learning session and in the evening between 6 and 7 p.m. The products under study are dissolved in distilled water. The products under study are administered at doses of 0.25 mg/kg/day.

RESULTS:

The test demonstrates that some products of the invention significantly decrease the number of failures to escape, reflecting, for the products of the invention, a strong antidepressant type activity.

Example F: Study of Anxiolytic Activity—So-called Light/Dark Cage Test in Mice

PRINCIPLE:

It is our intention to study the anxiolytic effects of the compounds of the invention by means of the so-called light/dark cage test in mice.

PROTOCOL:

This test was developed by Crawley et al. (1981, Pharmacol. Biochem. Behav. 1981, 12 (5), pp 695–9), then modified and behaviorally validated. The test involves two cages of equal size (20×20×14 cm) made of PVC. One is strongly illuminated by a 100 W lamp ("cold" light), the other is made dark. The two cages are separated from one another by means of a small opaque tunnel (5×7 cm). The mice are introduced individually into the illuminated cage, and as soon as they have entered the dark cage for the first time, the time spent by the animals in the illuminated cage and also the number of transits between the dark cage and the illuminated cage are recorded over 5 minutes by means of keyboards connected to a computer.

Each experimental group comprises at least 15 animals.

RESULTS:

The intraperitoneal administration of the products of the invention leads to an increase in the time spent by the mice in the illuminated cage and the number of transits between the dark cage and the illuminated cage.

This significant increase in the two parameters studied shows the exceptional anxiolytic activity of the compounds of the invention.

Example G: Pharmaceutical Composition

Tablets containing a 5 mg dose of n-indan-2-yl-8-(2-aminoethoxy)thiochroman

| Formula for 10,000 tablets: | |
|---|---|
| N-Indan-2-yl-8-(2-aminoethoxy)thiochroman | 50 g |
| Wheat starch | 75 g |
| Maize starch | 75 g |
| Lactose | 325 g |
| Magnesium stearate | 10 g |
| Silica | 5 g |
| Hydroxypropylcellulose | 10 g |

We claim:

1. A compound selected from those of formula (I):

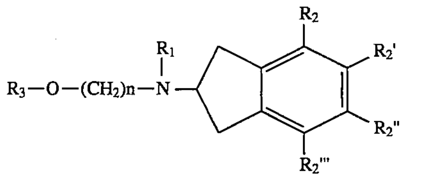

(I)

in which:

$R_1$ represents hydrogen or a radical selected from the group consisting of unsubstituted or substituted alkyl, cycloalkyl, cycloalkylalkyl, unsubstituted or substituted phenyl, and unsubstituted or substituted phenylalkyl, $R_2$, $R_{2'}$, $R_{2''}$ and $R_{2'''}$ represent, independently of one another, hydrogen or a radical selected from the group consisting of halogen, unsubstituted alkyl, substituted alkyl, unsubstituted alkoxy, and substituted alkoxy, n represents an integer of 1 to 6, inclusive $R_3$ represents a group of formula (A):

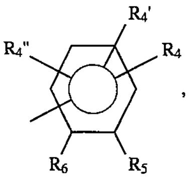

, (A)

in which:

$R_4$, $R_{4'}$ and $R_{4''}$ represent, independently of one another, hydrogen or a radical selected from the group consisting of halogen, unsubstituted alkyl, substituted alkyl, unsubstituted alkoxy, and substituted alkoxy, $R_5$ and $R_6$, together with the benzene ring which carries them, form a ring system $E_1$ selected from the group consisting of indene, naphthalene, benzothiophene, benzofuran, indole, benzimidazole, benzopyran, benzothiopyran, chroman, thiochroman, quinoline, isoquinoline, indazole, 2,3-dihydro-1,4-benzodithiin, quinoxaline, quinazoline, cinnoline, benzothiazole, benzisothiazole, benzoxazole, benzisoxazole, 2,3-dihydro-1,4-benzoxathiin, 1,4-benzoxazine, 1,4-benzothiazine, 1,3-benzodioxole, 1,3-benzodioxane, 1,4-benzodioxane, and 1,4-benzodioxin, on the understanding that the portion of the ring system $E_1$ formed by $R_5$ and $R_6$ and the 2 carbon atoms of the benzene ring which carry them is:

unhydrogenated or partially hydrogenated, and unsubstituted or substituted with one or more radicals selected from the group consisting of halogen, hydroxyl, lower alkyl, unsubstituted alkoxy, substituted alkoxy, lower alkoxycarbonyl, and carboxyl, on the understanding that, except where otherwise stated, the terms "alkyl" and "alkoxy" mean linear or branched groups containing 1 to 6 carbon atoms, inclusive, the term "substituted" associated with "alkyl" and "alkoxy" radicals means "substituted with one or more radicals selected from the group consisting of halogen, hydroxyl, and alkoxy", the term "cycloalkyl" denotes a cyclic group having 3 to 8 carbon atoms, inclusive, the term "substituted" associated with "phenyl" and "phenylalkyl" radicals means that these radicals are substituted on the phenyl ring with one or more substituents selected from the group consisting of halogen, alkyl, alkoxy, hydroxyl, and polyhaloalkyl, and an optical isomer and also an addition salt thereof with a pharmaceutically-acceptable acid or base.

2. A compound as claimed in claim 1, in which $R_5$ and $R_6$, together with the benzene ring which carries them, form a ring system $E_1$ selected from the group consisting of naphthalene, benzopyran, benzothiopyran, chroman, thiochroman, and benzodioxane.

3. A compound as claimed in claim 1 which is selected from 8-{4-[(n-indan-2-yl)amino]butyloxy}thiochroman or an addition salt thereof with a pharmaceutically-acceptable acid.

4. A compound as claimed in claim 1 which is selected from 8-{3-[(n-indan-2-yl)amino]propyloxy}thiochroman or an addition salt thereof with a pharmaceutically-acceptable acid.

5. A compound as claimed in claim 1 which is selected from 8-{2-[(n-indan-2-yl)amino]ethoxy}thiochroman or an addition salt thereof with a pharmaceutically-acceptable acid.

6. A compound as claimed in claim 1 which is selected from 8-{3-[(n-propyl-n-indan-2-yl)amino]propyloxy}thiochroman or an addition salt thereof with a pharmaceutically-acceptable acid.

7. A compound as claimed in claim 1 which is selected from 5-{2-[(n-indan-2-yl-)amino]ethoxy}-1,4-benzodioxane or an addition salt thereof with a pharmaceutically-acceptable acid.

8. A pharmaceutical composition containing a compound of claim 1, or one of its physiologically-tolerable salts, in combination with one or more pharmaceutically-acceptable excipients or vehicles.

9. A method of treating a mammal afflicted with a disorder associated with 5-$HT_{1A}$ or 5-$HT_{2C}$ receptors comprising the step of administering an amount of a compound of claim 1 which is effective for alleviating said condition.

10. A method of claim 9 wherein the disorder is selected from the group consisting of anxiety and depression.

* * * * *

UNITED STATES PATENT AND TRADEMARK OFFICE
CERTIFICATE OF CORRECTION

PATENT NO. : 5,569,669  Page 1 of 2
DATED : October 29, 1996
INVENTOR(S) : G. Guillaumet; M. Viaud; P. Renard; G. Adam; D. Caignard; B. Lemaitre; M. Rettori It is certified that error appears in the above-indentified patent and that said Letters Patent is hereby corrected as shown below:

Column 3, line 8: "$R_4''$ " should read -- $R_{4''}$ --.

Column 3, line 23: "$R_4''$ " should read -- $R_{4''}$ --.

Column 3, line 43: "$_{R2}''$," "$R_2''',$" and "$_{R4}'',$" should read -- $R_{2''}$ --, -- $R_{2'''}$ -- and -- $R_{4''}$ --.

Column 3, line 48: "$R_1'-X''$(VI) should read -- $R_1'$ -X" --; "(VI)" should be at the right margin.

Column 3, line 60: "$R_1$ ." should read -- $R_{1'}$, --.

Column 6, line 7: "$CH_2S$;" at beginning of the line should be deleted. Page 9, line 17

Column 6, line 48: "[(n-indan-" should read -- [(N-indan- --.

Column 13, line 13: "N,n-" should read -- N,N- --.

Column 13, line 29: "METHYL" should read -- methyl -- (to be consistent with the rest of the title).

Column 13, line 34: "cm 3" should read -- $cm^3$ --.

UNITED STATES PATENT AND TRADEMARK OFFICE

CERTIFICATE OF CORRECTION

PATENT NO. : 5,569,669

DATED : October 29, 1996

INVENTOR(S) : G. Guillaumet; M. Viaud; P. Renard; G. Adam; D. Caignard; B. Lemaitre; M. Rettori It is certified that error appears in the above-indentified patent and that said Letters Patent is hereby corrected as shown below:

Column 18, lines 1&2; 5&6; 9&10; 13&14; 17&18: Delete "selected from" in each line.

Column 18, lines 2, 6, 10, and 18: "[(n-indan-" should read -- [(N-indan- -- in each line.

Column 18, line 14: "[(n-propyl-n-" should read -- [(N-propyl-N- --; delete unnecessary space in line.

Signed and Sealed this

Eighth Day of April, 1997

Attest:

BRUCE LEHMAN

Attesting Officer

*Commissioner of Patents and Trademarks*